United States Patent [19]
Begun et al.

[11] Patent Number: 5,474,090
[45] Date of Patent: Dec. 12, 1995

[54] EXERCISE MONITORING SYSTEM CAPABLE OF SIMULTANEOUS TRANSMISSION OF VOICE AND PHYSIOLOGICAL DATA

[75] Inventors: S. J. Begun, Cleveland Heights; Lambert Haner, Rocky River; Timothy Louis, Berea; John E. Trybuski, Parma, all of Ohio

[73] Assignee: The Scott Fetzer Company, Westlake, Ohio

[21] Appl. No.: 687,783

[22] Filed: Apr. 19, 1991

Related U.S. Application Data

[63] Continuation of Ser. No. 297,063, Jan. 13, 1989, abandoned.

[51] Int. Cl.$^6$ .................................................... G06F 15/38
[52] U.S. Cl. ............................ 128/707; 370/76; 379/106; 482/1
[58] Field of Search ............................. 370/109–110, 76, 370/110.1, 60, 69.1; 364/413.04; 379/106, 109, 102; 128/60, 904

[56] References Cited

U.S. PATENT DOCUMENTS

| | | | |
|---|---|---|---|
| 3,436,487 | 4/1969 | Blane | 370/7.6 |
| 3,882,277 | 5/1975 | DePedro et al. | 128/904 |
| 4,523,311 | 6/1985 | Lee et al. | 370/69.1 |
| 4,586,174 | 4/1986 | Wong | 370/69.1 |
| 4,757,495 | 7/1988 | Decker et al. | 370/69.1 |

FOREIGN PATENT DOCUMENTS

| | | | |
|---|---|---|---|
| 705727 | 9/1987 | WIPO | G06F 15/42 |

OTHER PUBLICATIONS

"Automated Information Systems in Quality Assurance" Nursing Economics, Jan./Feb. 1987.
"Proceedings of Annual Conference of IEEE Eng . . . ", vol. 314 4 Nov. 1988, pp. 1326–1327, Murari, Kejariwal et al. Transtelephone Electrocardiogram and voice signal Transmitter–Receiver system.
"Transtelephone For Remote Cardiac", Jane Howard et al. Medical Elec., Jun. 1987, pp. 90–94.

*Primary Examiner*—Gail O. Hayes
*Attorney, Agent, or Firm*—Watts, Hoffmann Fisher & HeinkeCo.

[57] ABSTRACT

Apparatus and method for monitoring exercise activity and exercise responses of a user/patient. The monitoring apparatus and method forms the basis of a physical fitness system or a patient rehabilitation system for rehabilitating cardiac, orthopedic or other patients that require physiological monitoring during a therapy session. The system includes a patient station which in the case of cardiac rehabilitation includes an ECG monitor and a transmitting unit for transmitting ECG data and patient speech signals over a voice grade phone line. A base unit, located at a remote location, receives a composite analog signal containing the ECG data and voice signal and includes signal processing devices for separating the signal and for continuously storing the ECG data on a mass storage device for the entire therapy session. At the conclusion of the therapy session, selected portions of the stored ECG data can be transferred to a removable storage medium such as a floppy disk. The base station includes means for transmitting commands in the form of DTMF tones to the patient station to initiate the therapy session and/or to control the work load of an exercise device being used by the patient. Patients are connected to the patient transmitting unit by a fiber optic or RF link. The ECG data is transmitted in a 2170–2370 Hz. frequency band using frequency modulation on a carrier of substantially 2270 Hz. Notch and band pass filters remove the selected frequency band from the voice signal.

33 Claims, 14 Drawing Sheets

EXERCISE MONITORING SYSTEM CAPABLE OF SIMULTANEOUS TRANSMISSION OF VOICE AND PHYSIOLOGICAL DATA

This application is a continuation of application Ser. No. 07/297,063, filed Jan. 13, 1989, abandoned.

TECHNICAL FIELD

The present invention relates generally to physiological data monitoring and in particular to a system for monitoring an exercise session of well persons or an exercise session forming part of a rehabilitation program for cardiac, orthopedic and other patients requiring physiological monitoring (such as ECG data monitoring) during a physical therapy procedure.

BACKGROUND ART

The monitoring of physiological data during an exercise session is desirable for many applications. In the case of a physical fitness program the monitoring of the participant's vital signs such as heartbeat, breathing, etc. can provide an indication of the level of exertion that the participant is achieving. By monitoring the physiological data, a supervisor of the exercise session can insure that the participant is not over exerting himself or herself. The supervisor can also insure that the exercise level of the participant is at an adequate level for his or her physical condition.

After in-hospital treatment, cardiac or orthopedic patients are normally required to participate in a rehabilitation program that includes physical exercises normally conducted under supervision of a therapist or other medical personnel. The therapist in cooperation with the treating doctor establishes what needs to be done to improve a patient's mobility after surgery and to strengthen the patient after a heart attack so that he or she can return to a normal life as soon possible. Under current programs, the coronary patient is forced to return to the hospital periodically to engage in a rehabilitation procedure. Typically this involves the patient using an exercise device such as an exercise bicycle while being monitored by a therapist. In general, monitoring is provided by ECG electrodes attached to the patient. The ECG data are transmitted to a local monitoring station via wire or more commonly by an RF (radio frequency) transmission link. In particular, the patient wears a transmitter which transmits the ECG data to a receiver at the monitor station. The data is displayed graphically on a screen forming part of the station. The therapist or operator visually monitors the ECG data as displayed on the screen. In some systems, the operator is in verbal communication with the patient and may instruct the patient to adjust his or her work output based on the data being received at the station. For example, the operator may instruct the patient to increase his or her work output by increasing his or her own effort or alternately by changing the load being applied by the exercise device. In the case of an exercise bicycle, the patient may be instructed to increase the loading of the cycle or alternately to increase his or her pedaling effort. As should be apparent, the equipment and professional time involved in a rehabilitation program can be very expensive. Moreover, patients can find it very inconvenient to travel back to the hospital several times a week for the rehabilitation therapy. It has been found, that this rather expensive equipment can be under utilized since many patients fail to return to the hospital for their appointed therapy session due to inconvenience or other factors.

Systems have been suggested for at least partially alleviating some of the above identified problems. For example, a system has been proposed for remotely monitoring a cardiac rehabilitation session. In the suggested system, the exercise device is located at a remote location such as the patient's home. The patient is connected to the monitoring station over a standard telephone line. The patient attaches the ECG electrodes to himself before beginning the session. The output of the electrodes are connected to an interface device that transmits the ECG data over a telephone line to the operator. In addition, the patient wears a head set by which the patient can communicate with the operator for at least a part of the therapy session. In the suggested system, the telephone line is used to transmit either ECG data or voice data but not both at any given moment in time.

DISCLOSURE OF THE INVENTION

The present invention provides a new and improved system for monitoring a user during an exercise session. The disclosed system includes the capability of concurrently transmitting user physiological data and user voice signals to monitoring personnel.

The disclosed system may be used to monitor the exercise of well persons such as might be desirable as part of a physical fitness program or the disclosed system may be used in the rehabilitating of patients requiring physical therapy such as cardiac and orthopedic patients. When used in the latter application, the system is designed to provide greater utilization of the equipment so that overall costs for rehabilitating patients are reduced on a per patient basis since a greater number of patients can be treated in a given time period as compared to currently available rehabilitation equipment.

According to the preferred embodiment of the invention, the system includes a base station at which an operator can monitor an exercise session being performed by one or more users (or patients in the case of rehabilitation system) and a user station which includes the exercise device and a unit for concurrently transmitting physiological data and a voice signal to the base station. The communication link may include means for transmitting work output of the user, blood pressure data and may also include means for transmitting control data to the exercise device in response to commands issued from the base station.

To facilitate the description, the invention will be described as it would be embodied in a patient rehabilitation system. It should be understood that the invention is adaptable to a wide variation of applications including physical fitness systems in general and the invention should not be limited to this particular application.

In the preferred and illustrated rehabilitation system embodiment, the patient station is linked by telephone if the patient station is at a remote location. The disclosed base station can also communicate with local patient stations, i.e., stations located within the hospital near the base station and the interconnection may include RF (radio frequency) links or hard wired links.

In the disclosed embodiment, the system is shown as comprising a patient unit located at a remote location that communicates with the base station over a voice grade telephone line. The system, however, is adaptable to a much wider application which may include clusters of remote patient stations interconnected and communicating with an intermediate hub which may be located in a hospital or other centralized location. The hub acts as a relay station and conveys the data received from the individual patient stations to which it is connected, to a base unit located at another location. The communication between the hub and the remote base station might be achieved over a dedicated, high quality phone line capable of transferring multiple data/voice signals.

This wide area application can make it cost efficient for remotely located hospitals such as small rural hospitals (which do not have the resources to provide their own rehabilitation system), to provide a rehabilitation program using the disclosed system. In this wide area application a hub would be installed at the rural hospital enabling it to communicate over local phone lines with its patients. The actual base unit, however, would be located at a remote location such as a hospital in a major metropolitan area. The base station could directly communicate with several hubs and as a result, large numbers of patients could be monitored with a single rehabilitation system. With this disclosed application, even greater utilization of the equipment could be realized further reducing the cost per patient for a rehabilitation program.

To further facilitate the description of the invention, the system will be disclosed in connection with an ECG monitoring application. It should be noted that the disclosed system can be used to monitor other physiological data such as frequency of breathing, minute ventilation, oxygen uptake, oxygen saturation, etc. and should not be limited to the disclosed ECG application.

In the preferred embodiment, for remote patient stations i.e. patient stations linked by telephone with the hospital base station, a fiber optics link is preferably used to connect the patient with the patient unit. The fiber optic link is used to transmit both the physiological data such as ECG data as well as voice signals to and from the patient. A fiber optic link is preferred because it is less expensive than an RF link and interference due to spurious electromagnetic radiation which could easily disrupt an RF link have minimal effect if any on a fiber optic link. In addition, a fiber optic link provides total electrical isolation between the patient and the telephone line which is desirable.

In the exemplary embodiment, the base station includes a computer including a monitor for displaying the ECG and other data received from the patient station. In the disclosed embodiment, the data for up to five patients can be concurrently displayed on the computer monitor. The computer is connected to a printer by which reports are generated summarizing data obtained during the therapy session. It should be noted that the system can be enlarged to accommodate more patients.

According to a feature of the invention, storage is provided at the base station to record all of the data generated during the therapy session. With the disclosed apparatus, data such as ECG rhythm charts or strips can be reviewed after the session is terminated. In addition, data can be edited so that only certain portions are transferred to more permanent storage such as removable magnetic media. In the preferred embodiment, data generated during the session is stored on a non-removable magnetic media normally termed a "hard disk". Following the session, all or selected portions of the data stored on the hard disk is transferred to floppy disks.

According to a feature of this embodiment, the system includes an algorithm for automatically storing physiological data that is considered abnormal. This is done without intervention of the operator. Provision is also made for the operator to flag physiological data as its being received and being displayed on the screen. For example, if ECG data is being monitored, the operator can designate ECG data currently being displayed, to be flagged so that it is automatically transferred to the floppy discs at the end of a patient's session. In addition, the system may include an arrhythmia detection procedure which, if activated, flags the ECG data that the system has detected as showing arrhythmia. This flagged data then is automatically transferred to the patient disc during a session editing procedure. The unit includes a signal discriminating device for detecting deviations from a normal signal. This enables the system to detect unusual or unexpected phenomenon and to flag and/or permanently record this data.

To facilitate the explanation of the invention, the system will be described in connection with the use of an exercise bicycle having an adjustable loading device. Exercise bicycles are currently available which have adjustable loading mechanisms which may include friction loaders, eddy current braking devices, hydraulic devices or other electromechanical devices. It should be understood, however, that the invention is adaptable to a wide variety of exercise devices and programs such as tread mills, rowing machines, weights, weight lifting machines, etc.

According to the invention, a patient station intended for remote use is disclosed which includes means for transmitting data as well as the patient's voice over a single, voice grade telephone line. In the preferred and illustrated embodiment, this is achieved by transmitting the data using frequency modulation at a audio frequency that is within the normal band width of a voice grade telephone line. The selected frequency band is filtered from the voice signal. In the illustrated embodiment, notch filters are employed to remove that component of the voice signal. The frequency for transmitting the data is selected to be one that does not appreciably affect the speech quality of the voice transmission if removed. For example, a frequency in the range of 2270 hz. will not appreciably affect the voice quality. This selected frequency forms a carrier for transmitting the ECG data from the patient station to the base station.

At the base station, filtering is again used to remove the data component from the voice signals so as not to substantially affect the voice signal heard by the operator. The data signal is then demodulated at the base station and the actual ECG data is then graphically displayed on the screen as well as stored by the storage device. With the disclosed invention, a simple and effective method and apparatus for transmitting both voice signals and data along a voice grade telephone line can be had.

According to a feature of this embodiment, data relating to work output or load of the exercise bicycle is transmitted with the ECG data. In particular, the data is encoded on the signal output by the ECG sensor. In addition, in a more preferred embodiment, control data issued by the operator for adjusting or modifying the work or load of the exercise device is transmitted along with the voice signal. The control signals are decoded at the patient station and are used to control a loading device such as an eddy current brake forming part of the exercise bicycle.

Additional features of the invention will become apparent and a fuller understanding obtained by reading the following detailed description made in connection with the accompanying drawings.

BEST MODE FOR CARRYING OUT THE INVENTION

Figure 1:
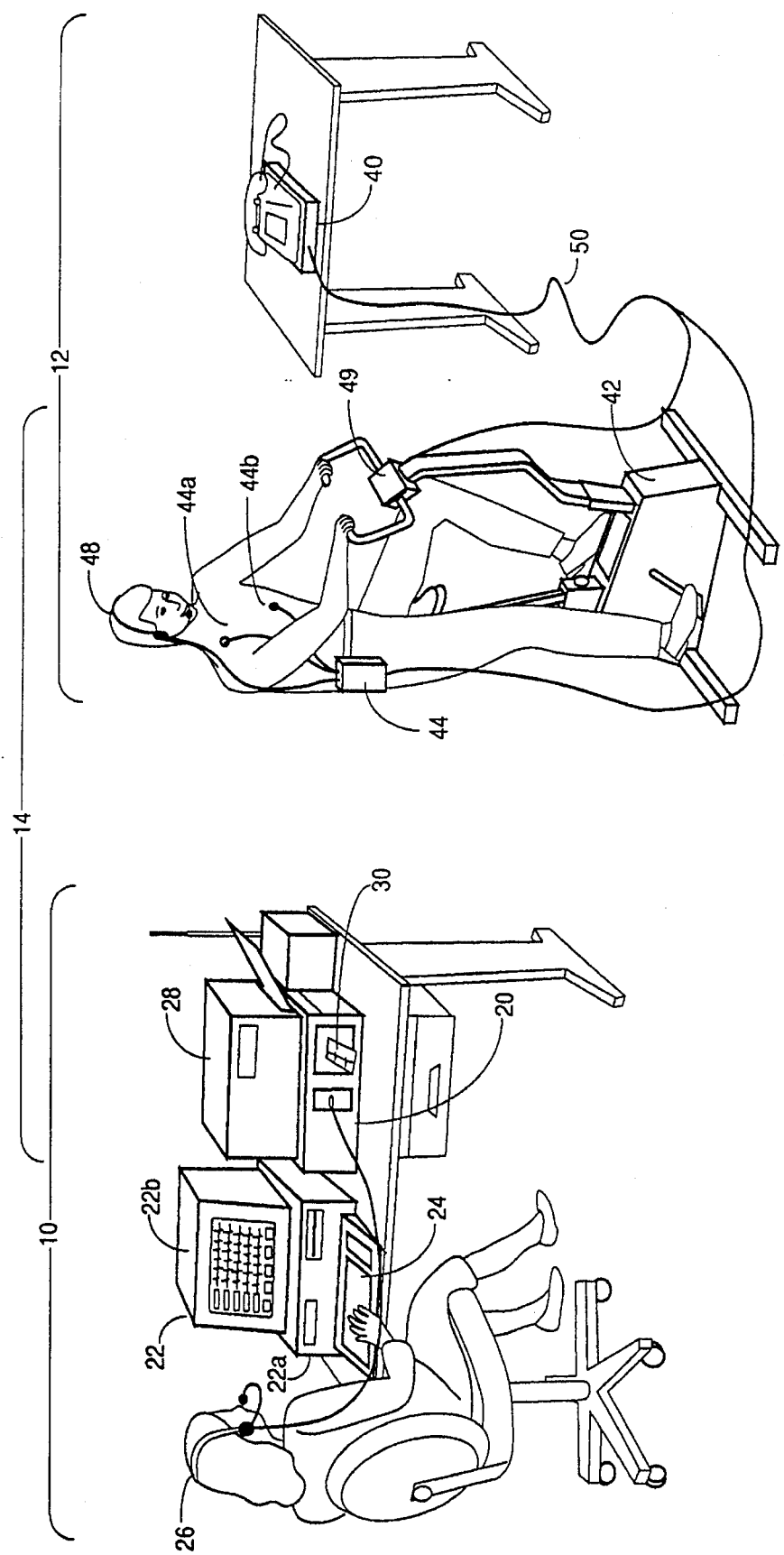
FIG. 1 is a perspective view of a cardiac rehabilitation system showing a base station and a patient station constructed in accordance with the preferred embodiment of the invention.
Figure 2A:
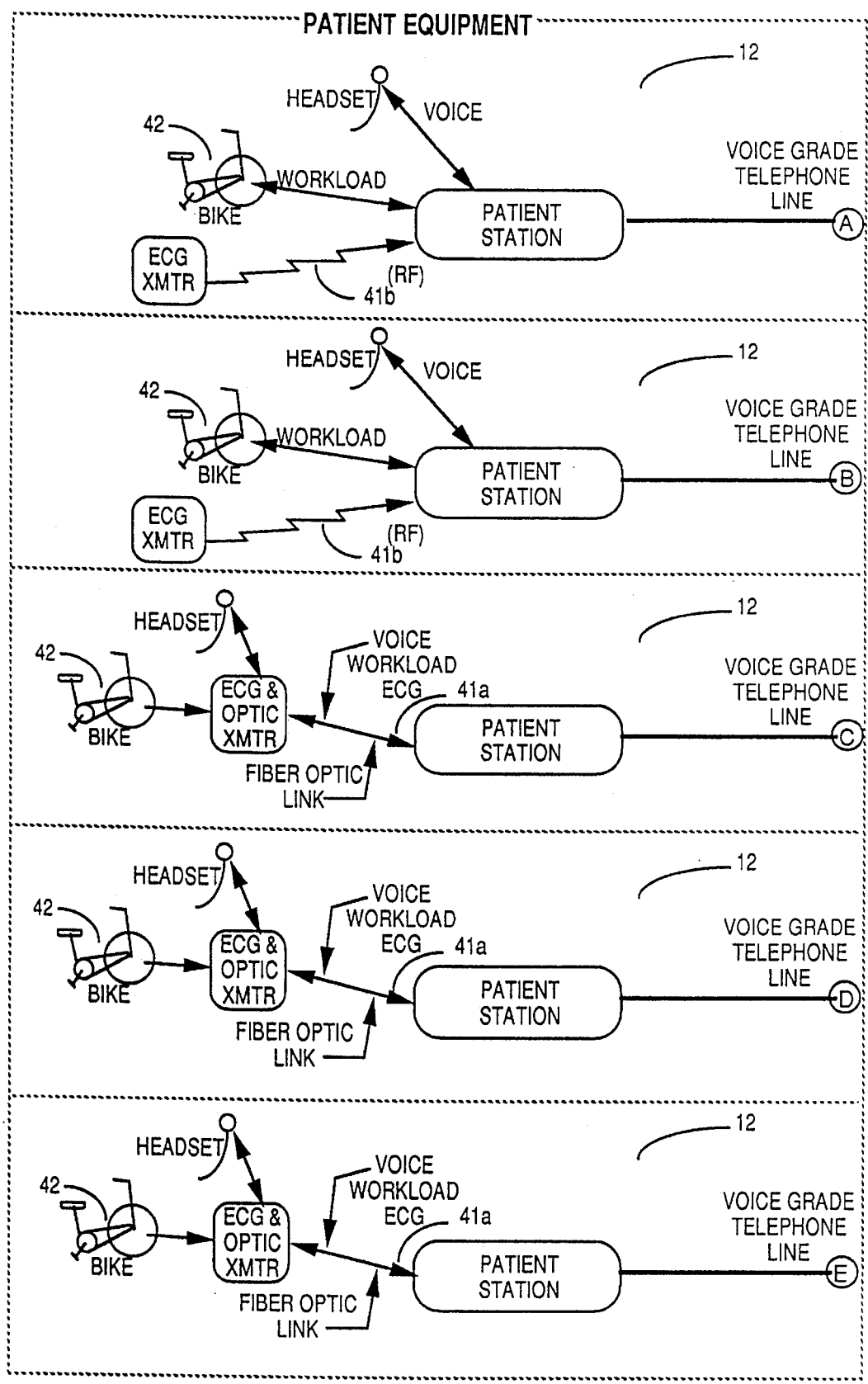
FIGS. 2a and 2b is a schematic representation of the cardiac rehabilitation system shown in FIG. 1.
Figure 2B:
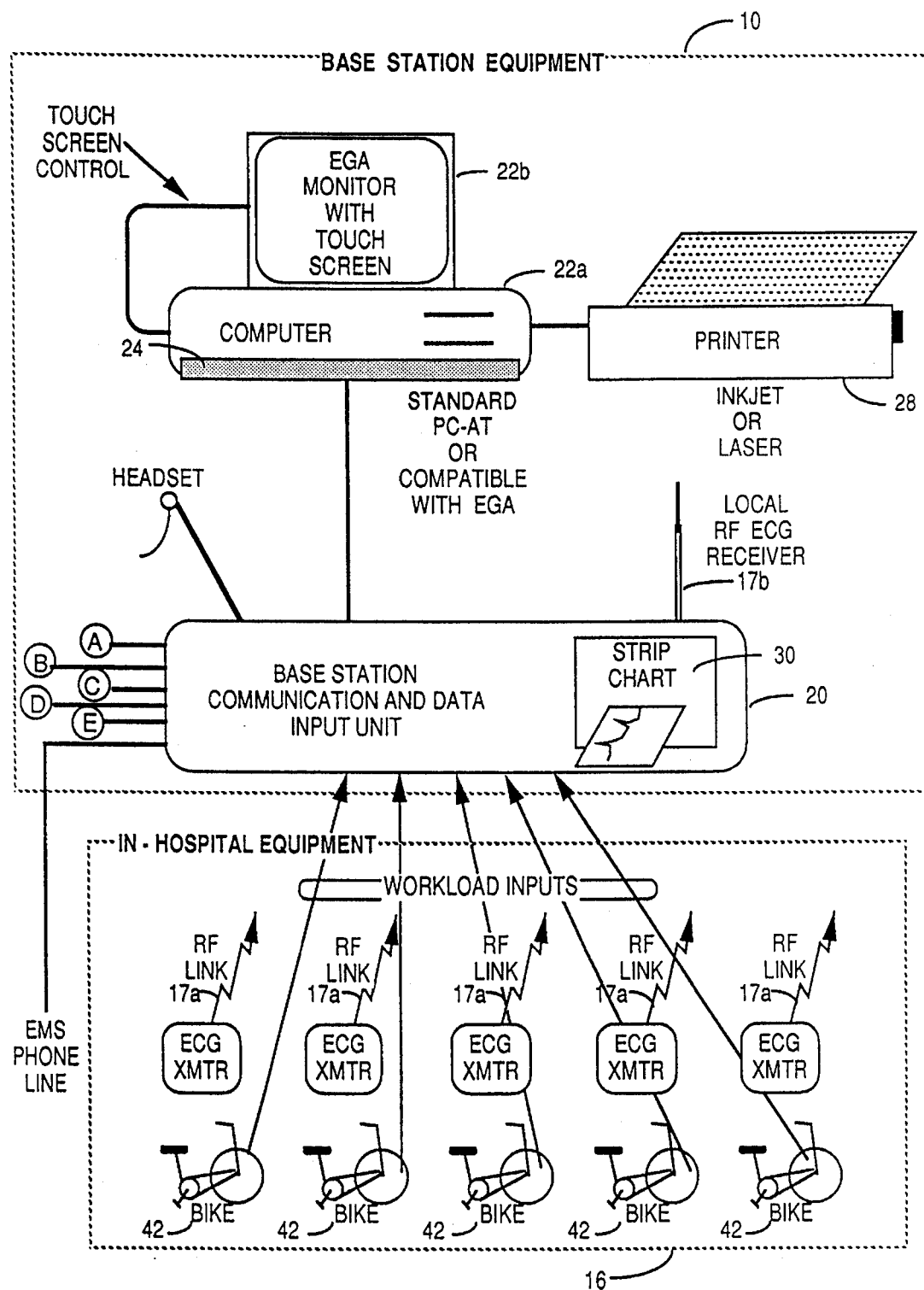

To facilitate the description as indicated above, the invention will be disclosed as it would be embodied in a cardiac rehabilitation system for rehabilitating cardiac patients. Referring to FIGS. 1 and 2, the overall cardiac rehabilitation system includes a base station 10 at which an operator or therapist sits and is preferably located in a hospital or other medical environment. The base station communicates with a patient station 12 located on site or off-site. The patient station when located off site, communicates with the base station over a voice grade phone line 14. When the patient station is located on site, communication with the base station may be achieved through phone lines or alternately through direct wire communication or over an RF (radio frequency) link including a transmitter 17a and a receiver 17b located at the base station 10. A schematic representation of an "on-site" or "in-hospital" station is shown in FIGS. 2a and 2b and indicated by the reference character 16.

The base station 10 includes a communication unit 20 which is connected to the phone line 14 and which receives and transmits data to the patient station. The communication unit 20 is connected to a patient monitoring terminal 22 and in the preferred embodiment comprises a computer processing unit (CPU) 22a and a display monitor 22b. A keyboard 24 is connected to the CPU 22a and is used by the operator to enter data, issue commands, and to exert other control functions over the base station. A printer 28 also forms part of the base station and is used to print reports summarizing the data obtained for a patient therapy session or summary of patient performance over a plurality of therapy sessions.

The therapist or operator, in the preferred embodiment wears a headset 26 by which the operator communicates with the patient over the same voice grade phone line 14. According to the invention, voice and data signals are transmitted concurrently along the phone line 14. The communication unit 20 preferably includes a strip chart recorder 30 which can be used to print ECG rhythm charts on demand during a therapy session.

The patient station includes a patient unit 40 which is connected to the telephone line 14. An exercise device such as an exercise bicycle 42 forms part of the patient station 12 and is used by the patient during the therapy session. In the disclosed embodiment, an ECG monitor indicated generally by the reference character 44 is worn or is attached to the patient and includes electrodes 44a, 44b that are directly attached to the patient and which monitor heart activity of the patient during the therapy session. The electrode information received by the ECG monitor 44 may be transmitted directly to the patient unit 40 by a wire link which preferably comprises a fiber optic link 41a or alternately through an RF (Radio Frequency) link 41b (shown in FIGS. 2a and 2b). In addition, the patient is in direct voice communication with the therapist at the base station via a headset 48 which is also connected to the patient unit 40. A sensor or other output device 49 for providing a signal indicative of the output of the exercise bicycle 42 is provided to the patient unit 40 over a wire 50.

In a more preferred embodiment, the wire 50 also provides a means for communicating control signals issued by the base station to the exercise bicycle to adjust the load being applied. For example, if the exercise bicycle 42 includes an eddy current brake, the wire 50 may communicate signals from the base station to adjust the braking level of the eddy current brake based on the information received at the base station from the ECG monitor 44.

Figure 3:
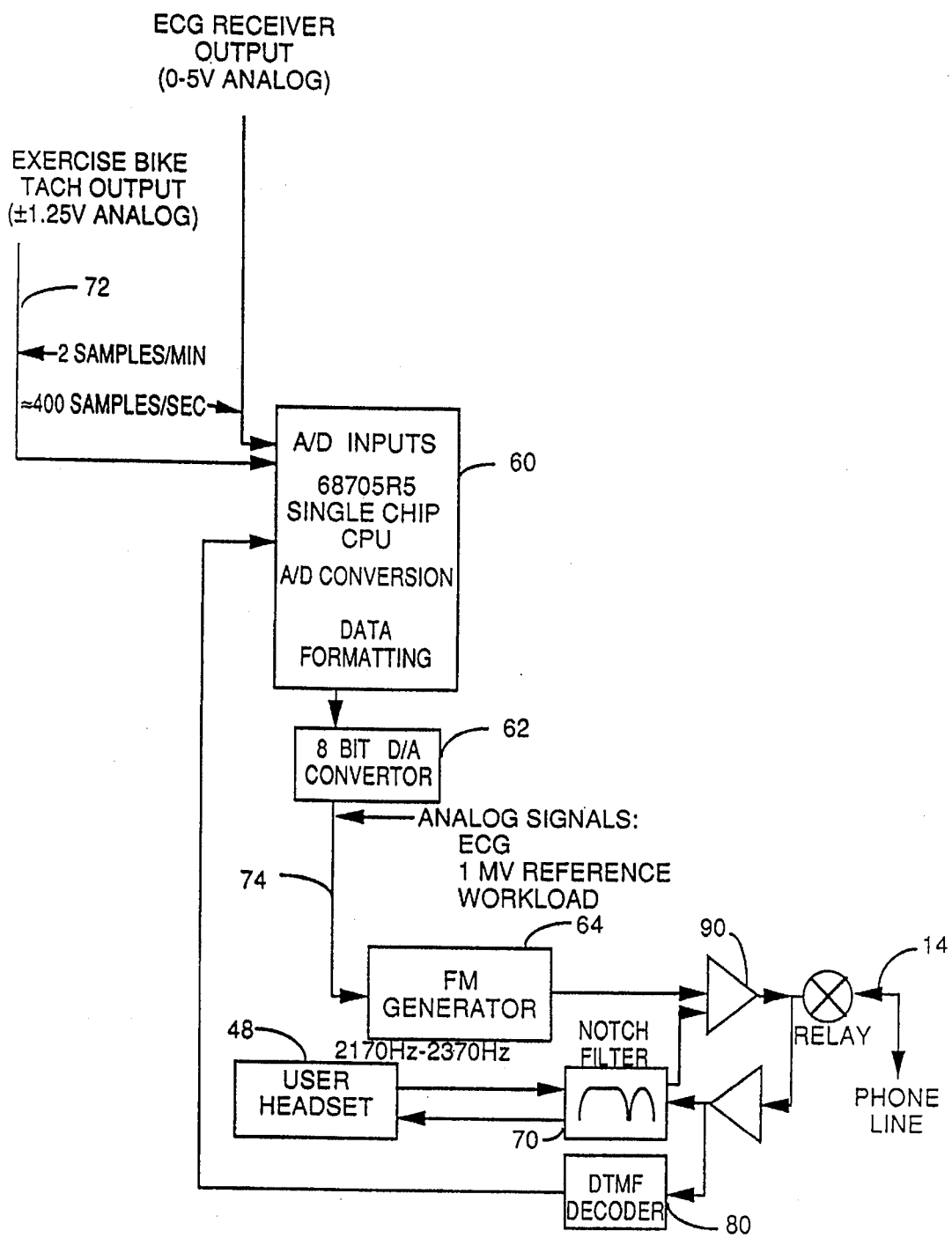
FIG. 3 is a schematic representation and block diagram of a patient unit forming part of the patient station.
Figure 4:
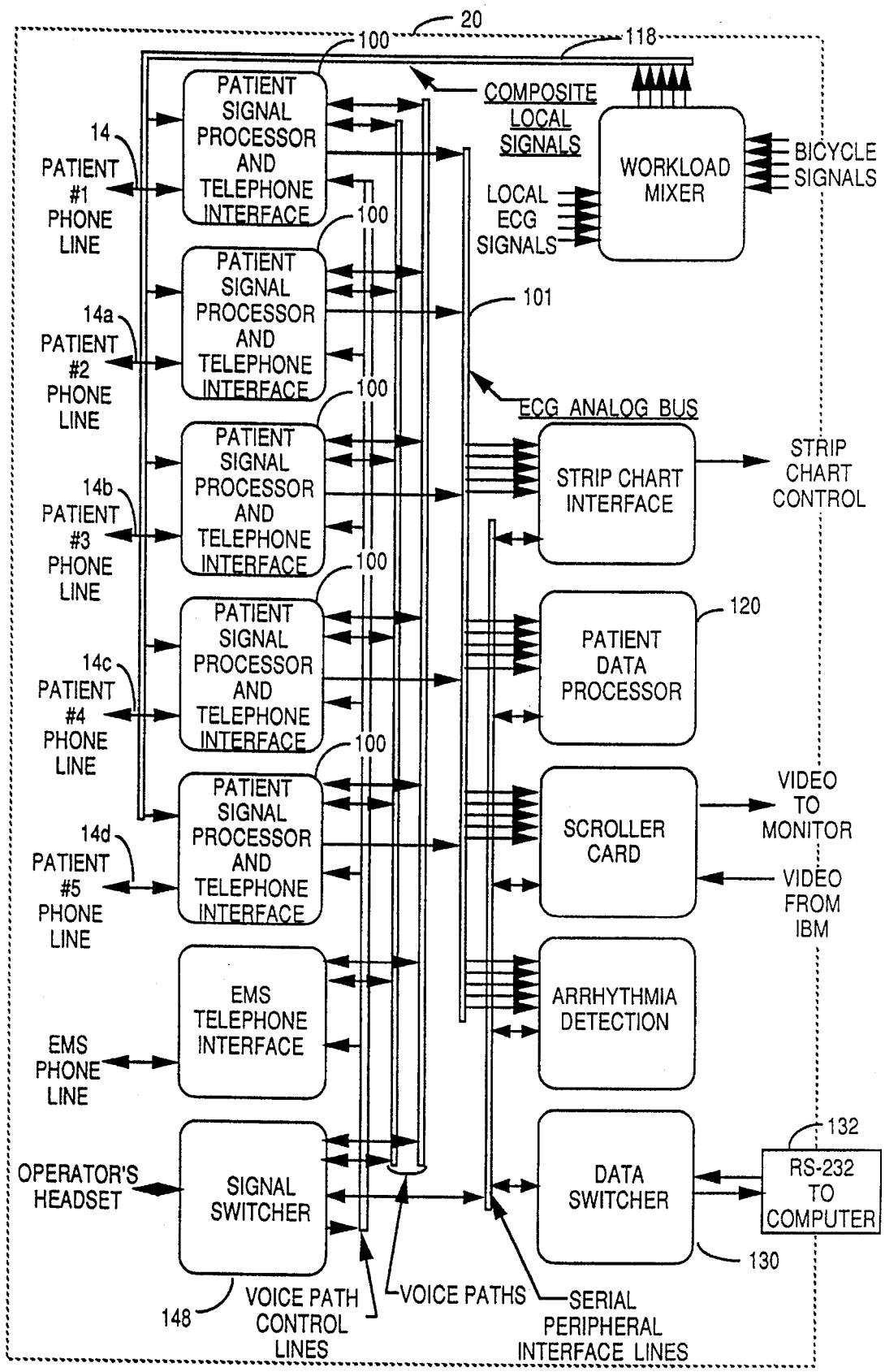
FIG. 4 is a schematic representation and block diagram of a base unit forming part of the base station.

Referring also to FIG. 3, the construction of the patient unit 40 is illustrated in block diagram form. A data receiver/converter 60 forms part of the patient unit 40 and receives work output data from the exercise bicycle and ECG data from the ECG monitor and converts and formats the data to a form that can be transmitted over the voice grade phone line 14. In the more preferred embodiment, the converter 60 is also used to format command data that it issued to the exercise bicycle to adjust its load. In the illustrated embodiment, a single chip CPU (micro-processor designated 68705R5, which is available from Motorola Inc., is used.

According to the invention, the ECG data is communicated as follows. The output of the ECG receiver (which typically varies between 0 and 5 volts analog) is sampled by the data converter 60 at the rate of 400 samples per second. The resulting digital output of the converter 60 is then passed through an 8 bit digital to analog converter 62 and is converted to an FM modulated signal using a voltage controlled oscillator 64. A frequency of substantially 2270 Hz is selected as the carrier frequency.

As is known, the band width of a voice grade telephone line is typically 400 Hz to 3400 Hz. It has been found that the ECG data signal emitted by the ECG monitor has a band width of approximately 100 Hz. In particular the ECG data signal varies between 0.05 Hz and 100 Hz. It has also been found by the inventor that removal of a 200 Hz frequency band of 2170 Hz to 2370 Hz from a voice signal will not substantially degrade the clarity or appreciably affect the quality of the voice transmission. In accordance with this feature of the invention, the telephone voice signal is passed through a notch filter 70 interposed between the telephone line 14 and the patient headset 48. As a result, the signal transmitted and received by the patient through the head set 48 has the frequency band 2170–2370 Hz removed from the transmission.

The selection of a carrier frequency of 2270 Hz takes into account various existing uses and signals in current voice grade phone lines. It has been found that signals in the range of 2600 Hz in conventional voice grade phone lines have been used or are used in intra office signaling systems. It has also been found that frequencies in the range of 3000–3400 Hz, if removed from the voice spectrum causes a substantial degradation in speech quality. In particular, it has been found that if frequencies in this range are removed from the voice signal, certain consonants are difficult to distinguish.

The output of the exercise bicycle is communicated to the data converter 60 along the line 72. In the illustrated embodiment, the output is sampled approximately two times per minute by the data converter. According to a feature of the invention, the exercise bicycle output data is encoded onto the same analog signal that transmits the ECG data. According to this feature, at approximately 30 second intervals, a one millivolt reference or pedestal signal is issued along the analog signal 74 line for approximately 50 milliseconds. Following this 50 millisecond pedestal signal a signal level representative of the output of the exercise bicycle is issued and is received, interpreted and stored at the base station.

According to a feature of the invention, command signals to initiate a monitoring session, end the monitoring session or to cause the patient unit to perform a function (such as change the work load or send work output data) are issued by the base station 10 and are transmitted along the phone line 14 and passed to the data converter 60. In the preferred embodiment, the command signals are standard DTMF (touch tone) signals that are decoded by a DTMF decoder 80. The decoded signals are then transmitted to the CPU 60. According to a feature of a more preferred embodiment, command signals to adjust the work output of the exercise bicycle that are issued by the base station are also transmitted along the phone line 14 in the form of DTMF signals that are decoded by the decoder 80 and passed to an exercise bicycle work load controller (not shown).

As seen in FIG. 3, the patient's speech information (after passing through the notch filter 70) is combined with the ECG signal by a summing circuit 90 and then is communicated to the phone line 14.

Referring also to FIGS. 4, 5a, 5b and 5c the patient unit 40 is connected to the base unit 20 by means of the phone line 14. As seen best in FIG. 4, the base unit 20 is capable of monitoring a plurality of phone lines 14–14d. In the illustrated embodiment, five remotely located patients can be monitored concurrently on five different phone lines 14–14d. Each phone line 14 is attached to a patient signal processor and telephone interface 100 forming part of the base unit 20.

Figure 5A:
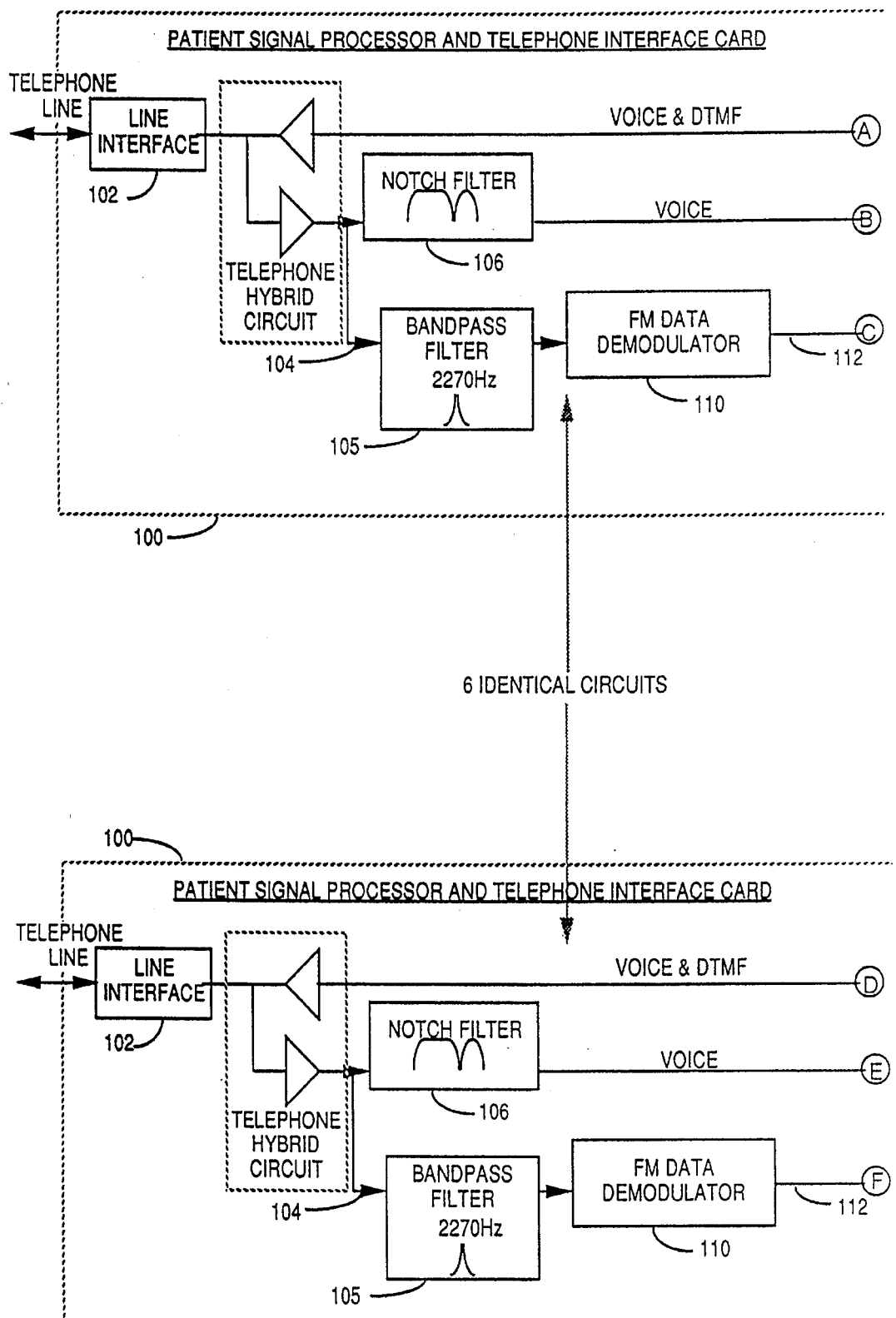
FIGS. 5a, 5b and 5c illustrate is a detailed block diagram of a patient signal processor/telephone interface card and a signal switcher card forming part of the base unit shown in FIG. 4.
Figure 5B:
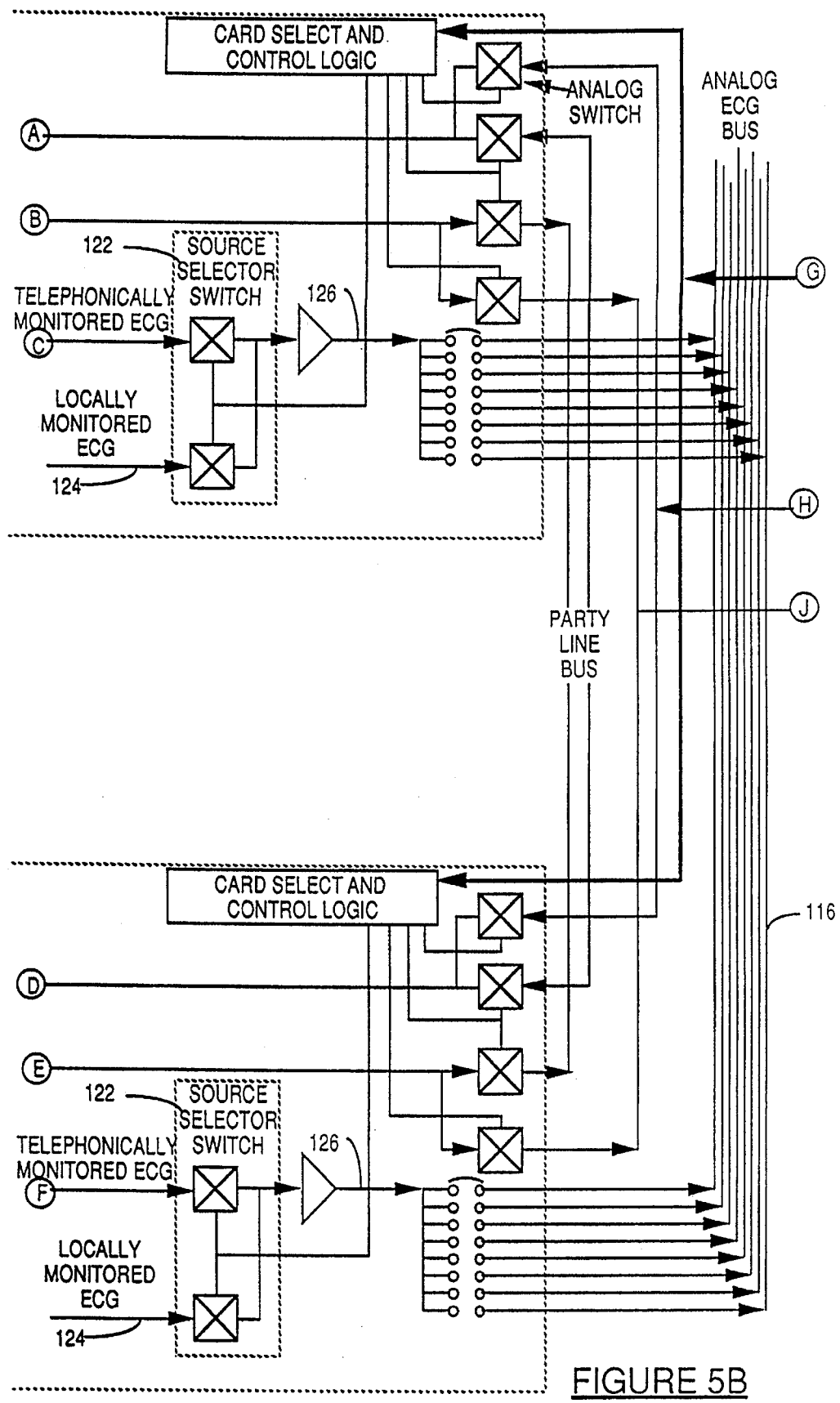
Figure 5C:
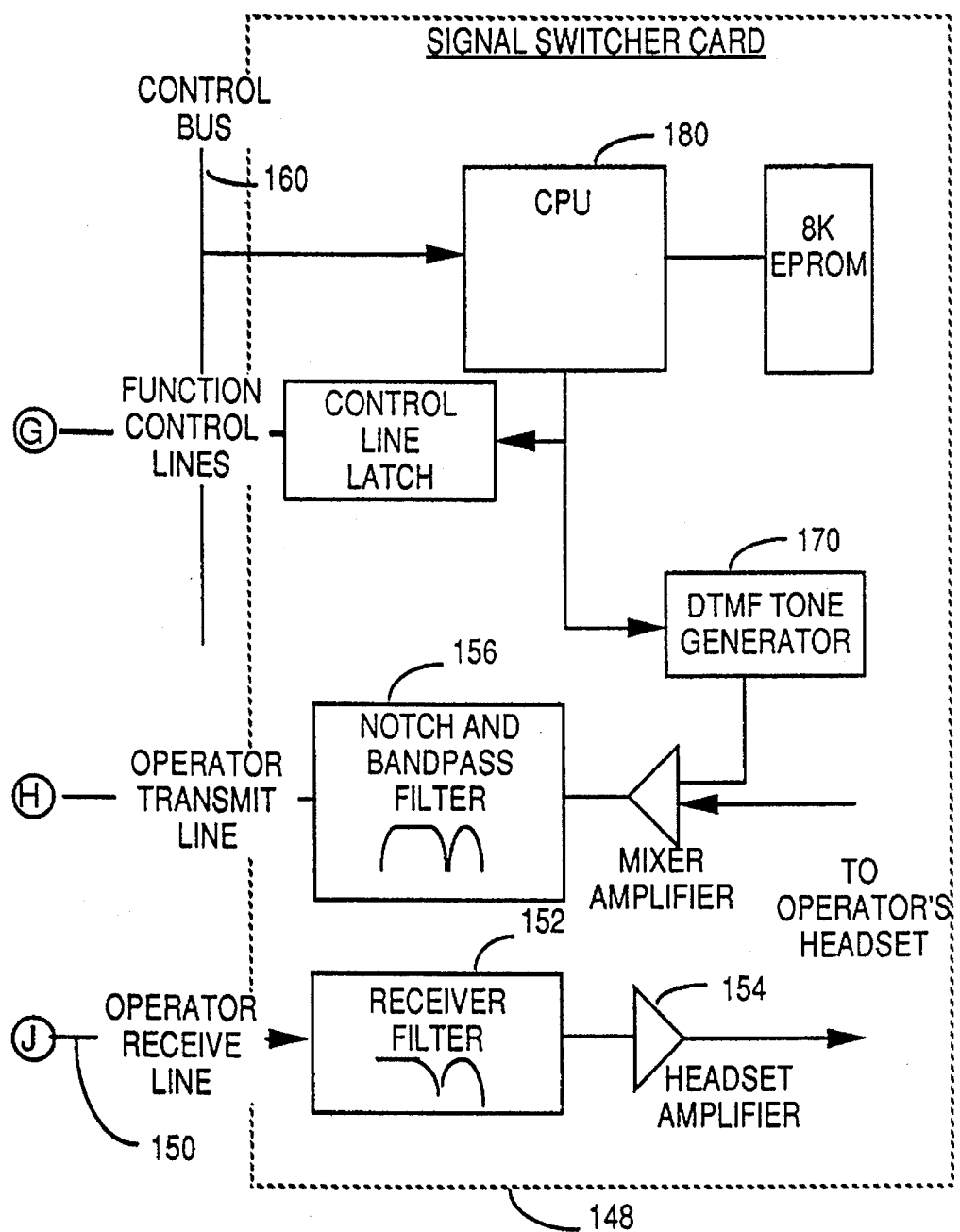

In the preferred embodiment, each patient signal processor and telephone interface represents a circuit card mounted within the base unit 20. Each card 100 includes a standard connection by which the telephone line 14 is connected to the card 14. Each card is connected via an edge connector to a signal bus 101 forming part of the base unit 20. The circuit functions provided by each patient signal processor and telephone card 100 are illustrated in FIGS. 5a, 5b and 5c. The telephone line 14 is connected to a line interface 102 and then to a telephone hybrid circuit which separates the incoming signal from the outgoing signal. The incoming signal which includes both voice and ECG data is passed along a signal line 104. The signal is passed through a notch filter 106, the output of which is the voice signal absent the ECG data signal which is carried by the 2170–2370 Hz band. The composite signal on the line 104 is also passed through a bandpass filter 105 which allows a frequency band of substantially 2170 HZ–2370 Hz to pass through. In other words, the speech component of the composite signal is removed. Thus, only the data component of the telephone signals is passed to an FM demodulator 110 leaving only the analog ECG data on an output line 112. This signal in turn is passed to an analog ECG bus 116 which communicates with a patient data processor 120 (shown in FIG. 4).

As indicated above, the base station 10 can communicate simultaneously with both local and remote patient stations. In accordance with this feature, each patient signal processor card 100 includes circuitry for receiving locally monitored ECG data. Referring in particular to FIGS. 5a, 5b and 5c each signal processor card 100 includes a source selector switch 122 which is operative to communicate either the line 112 (which conveys telephonically monitored ECG data) or a data line 124 to an output line 126. The locally monitored ECG data line 124 may be connected to an RF receiver forming part of an RF type ECG monitor or to other types of ECG monitoring devices used in hospital environments. The source selector switch 122, in the preferred embodiment, is a software controlled electronic switch, but alternately can comprise a manually operated switch.

The patient data processor 120 digitizes the analog signal data streams received from the patient signal processor cards 100 and conveys the data streams in serial fashion to a data switcher 130. This data is then communicated to a computer such as an Intel 80286/80386 based personal computer. Preferably, the connection is made to the computer via a standard serial RS-232 connection 132. Software, running in the computer, receives and manipulates the data received from the data switcher 130 and displays the data on the display screen 22b. In the preferred embodiment, ECG rhythm charts for all five patients being monitored are displayed concurrently on the screen. In addition, blood pressure, work output and other data monitored at the patient station is also displayed on the screen.

In the preferred embodiment, the system also includes a scroller card as part of the base unit 20 which enables the display unit 22a to display the patient data in real time which otherwise would be delayed if standard display cards/drivers normally found in personal computers were used.

As seen in FIGS. 4, 5a, 5b and 5c a signal switcher card 148 is connected to the operator's telephone headset 26 (shown in FIG. 1) and processes the voice signals sent and received by the operator. The voice signal from the patient station is transmitted along an operator receive line 150 and passed through a receiver filter 152 and headset amplifier 154 before traveling to the operator headset 26. The voice signal from the operator is passed through a notch and bandpass filter 156 to remove the frequency band 2170–2370 Hz which as explained above is a frequency band that is used to transmit ECG data from the patient. In addition, the signal switcher 148, responds to a control bus 160 and generates control signals using a DTMF tone generator 170 for controlling the activation of the patient unit 40. In a more preferred embodiment, DTMF encoded signals are used to adjust the load of the exercise bicycle 42. When the operator issues a command via the keyboard 24 or, alternately, if the command is issued automatically by the CPU in response to the ECG data, an on board CPU chip 180 sends an appropriate signal to the DTMF generator 170 which generates an appropriate control tone. The control tone is sent along the telephone line 14 and as explained above, is ultimately decoded by the DTMF decoder located at the patient station. The decoder 80 (FIG. 3) converts the tone signal to a command signal recognizable by the data converter 60 and/or the exercise bicycle load control. The signal switcher card 148 is also used to send the appropriate connect and disconnect signals to the patient station and to initiate and terminate the monitoring phase of the patient unit.

The blood pressure BP of the patient may be periodically monitored by the system or alternately the patient may measure his or her own blood pressure using a standard blood pressure measuring device. The BP data measured by the patient could be transmitted orally by the patient or transmitted electronically using a data input device such as a keyboard.

Figure 6A:
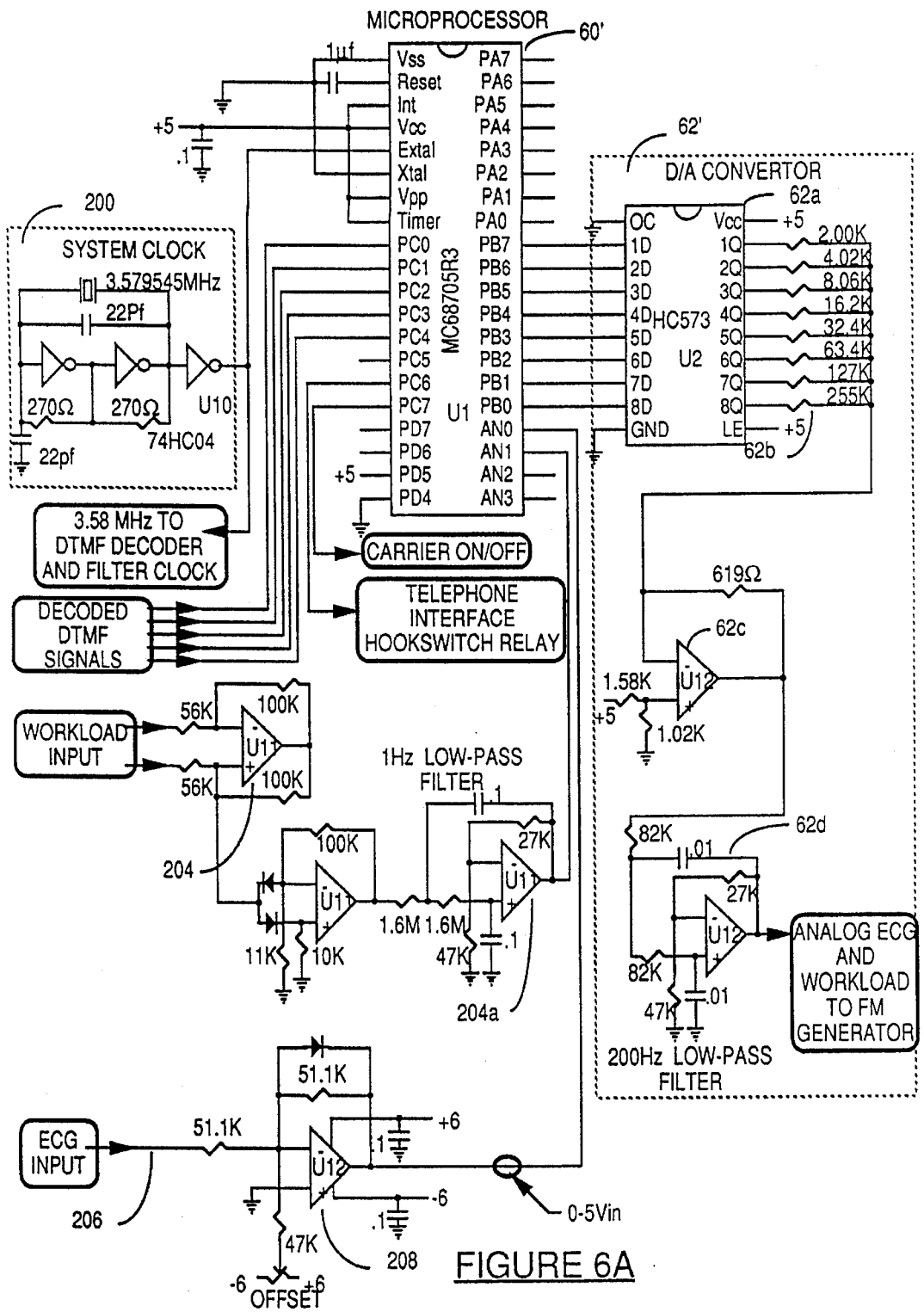
FIGS. 6a and 6b illustrate a detailed circuit schematic for the patient unit shown in block diagram form in FIG. 3.
Figure 6B:
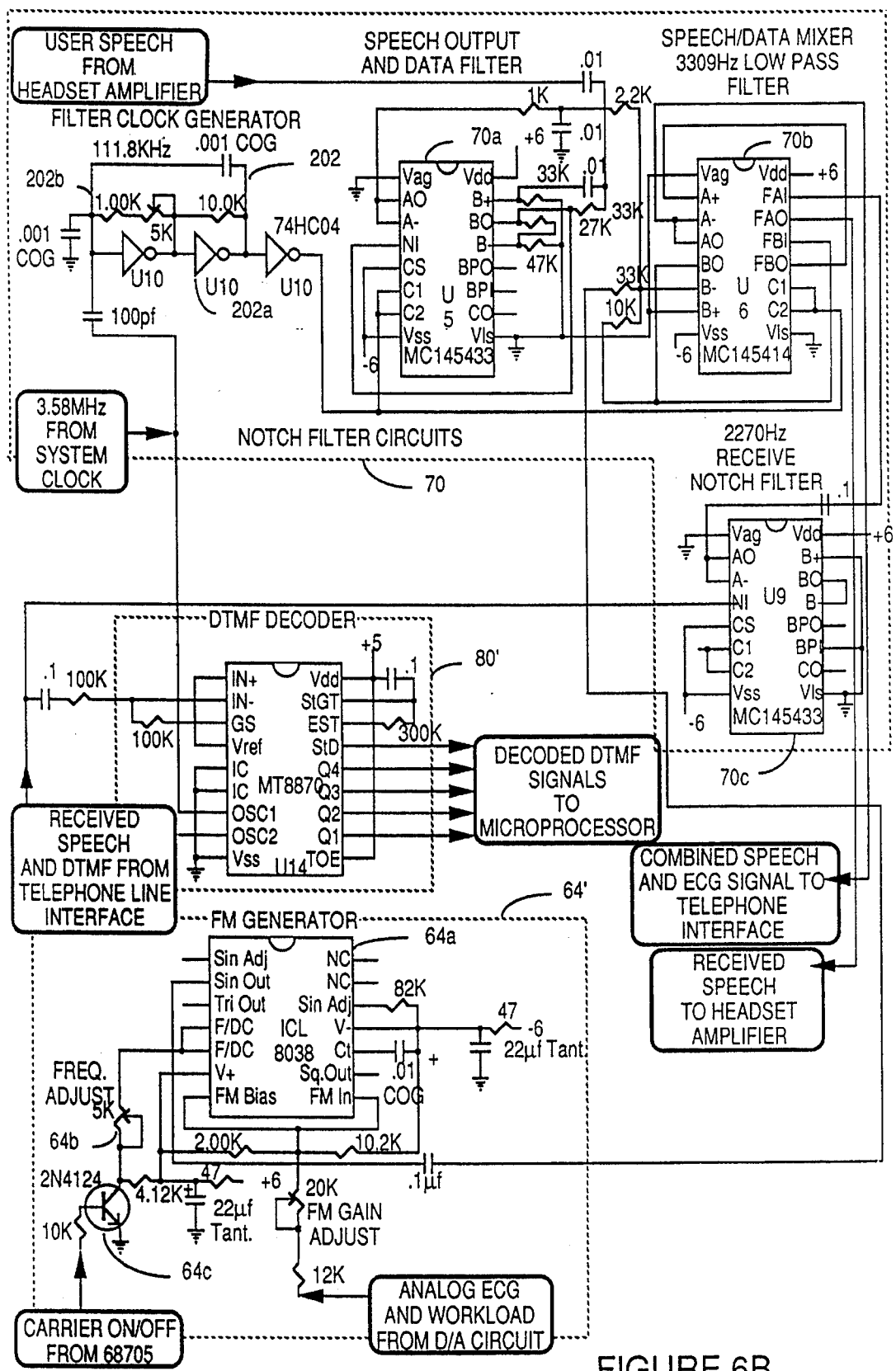

FIGS. 6(a) and 6(b) illustrate a more detailed schematic for the patient unit 40 (which is shown in block form in FIG. 3). Components in the schematic will be accorded the same reference character followed by an apostrophe (') as their corresponding components in the block diagram.

As indicated above, the patient unit 40 is controlled by a microprocessor 60' designated as an MC 68705R3 which is available from Motorola Inc. The 8 bit D/A (digital to analog) converter 62 in FIG. 3 is formed by a 74HC573 latch 62a interconnected with a resistor network 62b and conventional op-amp 62c as shown in FIG. 6a. The individual components are all available from various known sources. The D/A converter 62' also includes a 200 Hz low pass filter formed by an op-amp 62d and associated resistor/capacitor network which operates to smooth the analog signal output by the latch 62a and op-amp 62c.

The circuit for the patient unit 40 includes a system clock 200 which in the illustrated embodiment is formed using an inverter chip designated as a 74HC04 (available from various sources). A 3.579545 MHz crystal is used to generate a 3.58 MHz clock frequency which is communicated to the microprocessor 60' and a DTMF decoder 80' (shown in FIG. 6b). The DTMF decoder is available from Mitel Corporation and is designated as an MT8870. The decoder receives tones from the telephone line which correspond to commands issued by the base unit and decodes them into digital signals recognizable by the microprocessor 60'.

The ECG data and work load data are transmitted across the phone line as an FM (frequency modulated) signal. The FM generator 64' is formed by a voltage controlled oscillator 64a designated as an ICL 8038 which those skilled in the art will recognize as a general purpose voltage controlled oscillator that is available from various sources. The carrier frequency of 2270 Hz is selected by the choice of capacitors and resistors shown. The final frequency is adjusted by a frequency adjustment formed by potentiometer 64b. The resulting FM signal (with the ECG and work load data encoded) is passed to the notch filter 70'.

The notch filter indicated by the reference character 70 in FIG. 3 is actually formed by three (3) discrete components shown in FIG. 6b. In particular, the frequency band 2170 Hz–2370 Hz is removed from the patient speech signal by a speech output and data filter 70a which in the illustrated embodiment is formed by a notch/band pass filter designated as an MC145433 and available from Motorola Inc. The FM signal that is output from the FM generator is combined with the speech signal by way of a speech/data mixer 70b that is designated as an MC145414 and is also available from Motorola Inc. The resulting combined speech and ECG signal is conveyed to a conventional telephone interface (indicated by the reference character 90 in FIG. 3) and transmitted onto the phone line.

The incoming speech and DTMF codes (transmitted by the base station) are passed through the notch filter 70' and in particular through a 2270 Hz filter 70c designated as an MC145433 also available from Motorola Inc. The notch filter removes the frequency ban 2170–2370 Hz from the voice signal and passes the speech transmitted by the base station to the patient headset.

The components 70a, 70c of the disclosed notch/band pass filter 70' require a clock signal to determine the frequency band that will be passed by the filter components. According to the invention, the circuit includes a filter clock generator 202 (shown in FIG. 6b) for generating this necessary clock signal. In the disclosed embodiment, the clock generator 202 is formed by a multi-vibrator circuit using a series of inverters 202a and a RC circuit 202b to determine the clock frequency. According to the invention, the filter clock generator 202 is interconnected with the system clock 200 in order to minimize or eliminate heterodyning effects. In other words, the system is constructed so that the filter clock frequency is a sub-multiple of the system clock frequency. This is achieved by coupling the system clock signal to the filter clock generator 202 through a 100 PF capacitor. With this arrangement, the system clock 200 "drives" the filter clock 202 and in effect locks the frequency of the filter clock to the system clock.

According to the invention, the patient station transmission is activated upon receiving a predetermined DTMF code sent by the base station. The DTMF signal is decoded by the DTMF decoder 80' and as indicated above, sent to the microprocessor 60'. When the appropriate code is received by the microprocessor, a corresponding signal is output by the PC7 pin of the microprocessor 60' and turns on a transistor 64c designated as a 214124 which forms part of the frequency adjust circuit of the FM generator 64'. In short, the transistor 64c enables and disables the frequency adjust loop and in effect activates and de-activates the FM generator. By controlling the frequency adjust loop, however, it has been found that a smooth start-up of the FM generator achieved eliminating or minimizing noise heard by the patient or operator when the system is activated.

The output from the exercise device is communicated to a work load input 204. In the disclosed embodiment, the circuit is intended to receive a DC signal that may be either positive or negative depending on the direction of rotation of the exercise bicycle. For this reason, a full wave rectifier circuit is employed to ensure that regardless of the rotational direction, a positive signal is communicated to the microprocessor 60'. The input 204 also includes a 1 Hz low pass filter formed by an op-amp 204a and associated RC circuitry which removes noise from the input.

The output of the ECG monitor 44 (shown in FIG. 1) is communicated to an input line 206 which includes an offset adjust 208. In the disclosed embodiment, the input signal can vary between 0 and 5 volts and the offset adjust is used to adjust the input signal so that a 0 baseline corresponds to approximately 2.5 volts.

Figure 7:
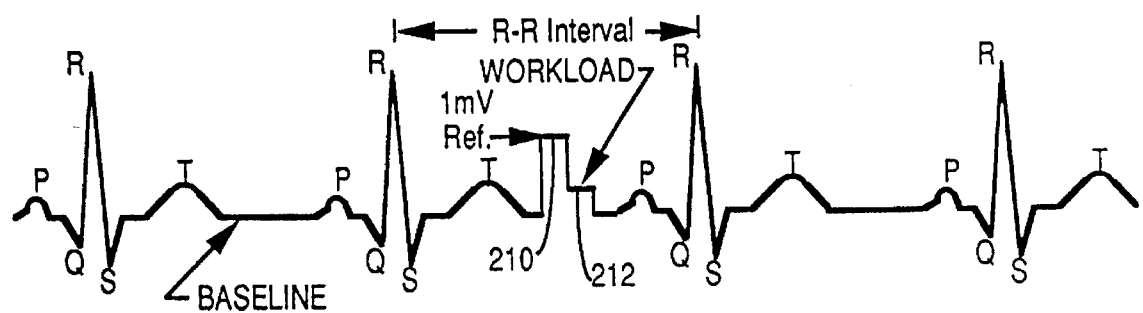
FIG. 7 illustrates an ECG waveform including other patient data that is encoded on the ECG signal and transmitted periodically along with the ECG data.

Referring to FIG. 7, a typical ECG rhythm chart or pattern is illustrated. As is known, the heartbeats are represented by a "QRS" wave, the extent of which is shown in FIG. 7. In addition, and as known, the pattern also includes what are known as P and T waves. The interval between heartbeats in known as the R-R interval.

According to the invention, data regarding work output and/or blood pressure is encoded on the ECG signal that is output from the patient unit. The ECG data and work load data are mixed by the microprocessor which in the preferred embodiment constantly monitors the R-R interval. When a command is received from the base station to transmit work load and/or blood pressure information or alternately, when a predetermined time interval, i.e., 30 seconds has elapsed, a reference "pedestal" 210 is issued by the-microprocessor preferably at a time calculated to be intermediate with the R-R interval. The pedestal signal 210 is issued for a predetermined amount of time, i.e., 50 ms. and is then followed by one or more stepped signals 212 that represent the work output of the bicycle or blood pressure. The base station includes means for detecting the pedestal and upon receiving the pedestal looks for and recognizes the work output/blood pressure related signal.

Figure 8A:
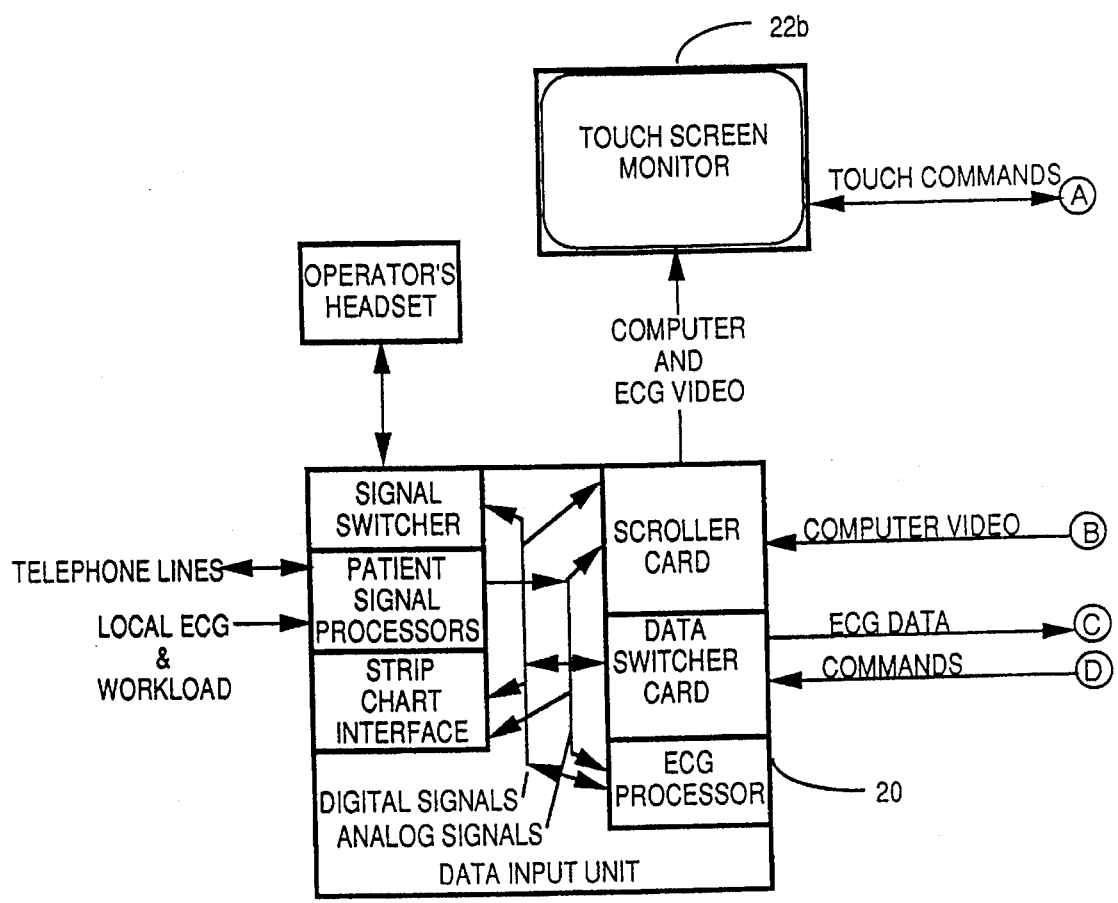
FIGS. 8a and 8b illustrate in block diagram format, various system functions performed by a computer based control unit; and, FIG. 9 is a block diagram of a more advanced embodiment of the invention that utilizes remote satellite hubs connected to a central base station.
Figure 8B:
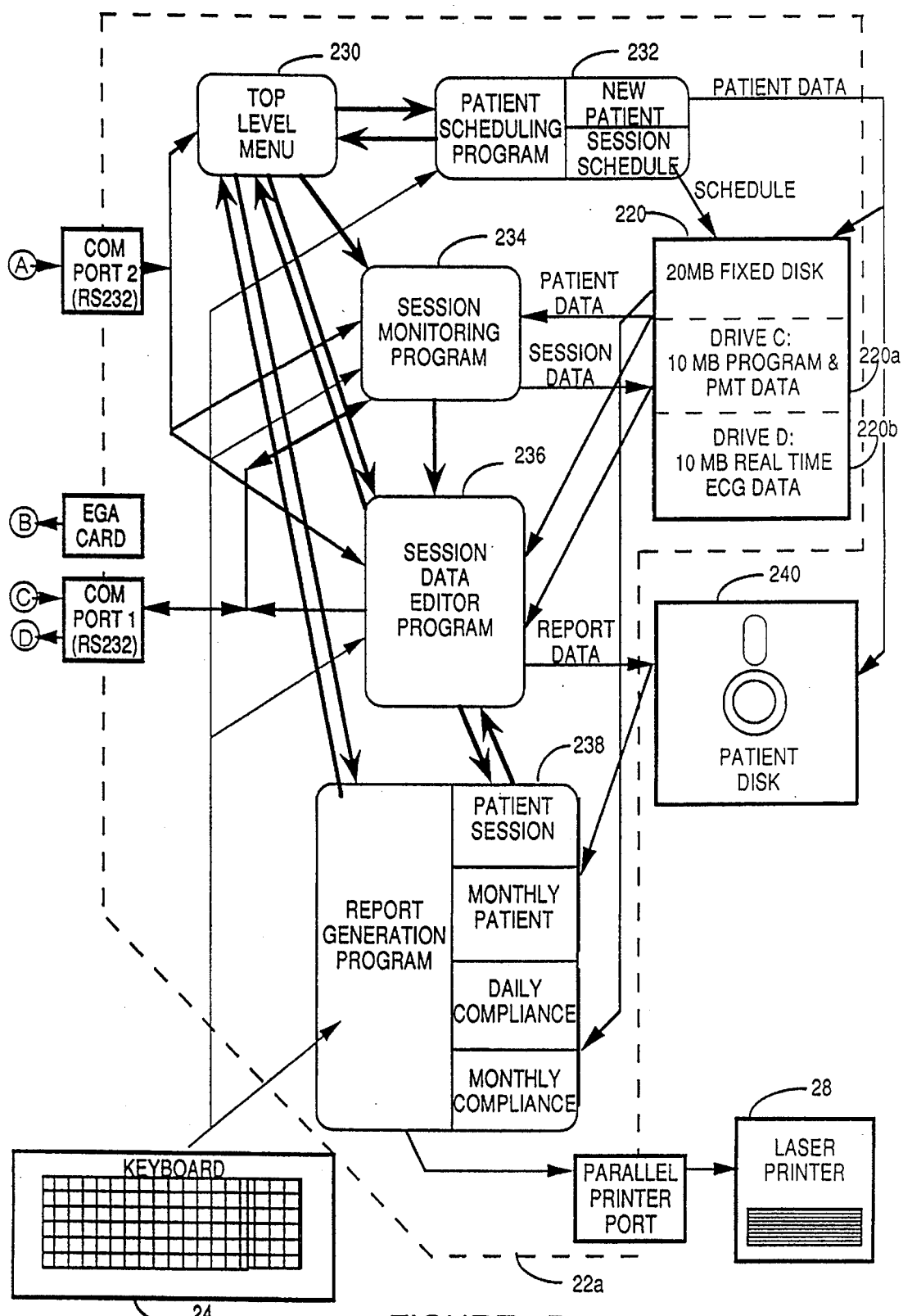

FIGS. 8*a*, and 8*b* illustrate is an overall system functional diagram which illustrates the interconnections and interfacing between the communication unit 20 and the monitoring terminal 22 (see also FIG. 1). Data between the communication unit 20 and the terminal 22, in the preferred embodiment, is transmitted across a serial connection. As seen in FIG. 8, in the illustrated embodiment, the link between the communication unit 20 and the terminal 22 is achieved through communication port which may use a standard RS 232 protocol. In the illustrated embodiment, the terminal 22 comprises an 80286 based personal computer (PC). Those skilled in the art will recognize this designation as one calling for a PC utilizing an 80286 microprocessor (available from Intel Corporation) or compatible microprocessor manufactured by another. Preferably, the unit is what is termed "AT" compatible (PC) which those in the art will recognize as a computer that is substantially similar in architecture to, and compatible with, an IBM AT (advanced technology) computer manufactured by the IBM Corporation.

During system use, the overall operation of the PC is controlled by one or more programs which are callable by the operator or alternately are called by other programs.

The physiological data received by the base unit is transmitted to the PC 22*a* over the serial interconnection (via communication port 1). The data may be checked, manipulated and/or processed by a control program running within the PC and is stored in a mass storage device 220 forming part of the PC 22*a*. In the preferred and illustrated embodiment, the mass storage device comprises what is termed a "fixed disk" or a "hard disk" which those in the art will recognize as describing a "Winchester Drive" having rigid magnetic media for storing data. In the preferred embodiment, two fixed disks 220*a*, 220*b* are employed. One disk 220*a* is used to store program and patient background data. The other disk 220*b* is used to store the physiological data during a therapy session as it is received from the base unit. It should be noted that the two disk drives 220*a*, 220*b* may actually comprise one large disk drive divided into two logical drives or alternately may actually comprise two separate physical drives. The purpose of having a separate drive for storing the physiological data as it is received during the session, is to minimize head movement by dedicating a hard drive or a portion of a large hard drive to receive and store only the physiological data.

In the preferred and illustrated embodiment the system control program includes a menu program indicated by the block 230 from which the various functions are selected by the operator. From the menu program 230, the operator may select a patient scheduling program 232, a session monitoring program 234, a session data editor program 236 and a report generation program 238.

The patient scheduling program 232 is used to set-up appointments and exercise prescriptions for patients and to generate permanent data for each patient. When a new patient is entered into the system, the patient scheduling program 232 opens a new file for that patient which may contain the name and address of the patient, his or her social security number, sex, age, hospital I.D., doctor, and other medical history information. This file is stored on the program hard disk 220*a*. The permanent patient data file is given a unique name by the system which may comprise a unique number for that patient or other alpha numeric designations. The file name may also be given a unique extension such as "PMT" to indicate to the system that that particular file is a permanent patient data file. The format for the filename is preferably "PATIENT#.PMT" where "PATIENT#" is any unique combination of alpha-numeric characters.

When a patient is to be logged onto the system for future therapy sessions, the system establishes a sessions protocol file that contains the parameters for that patient's therapy session. These parameters may include work load, session time and other parameters that are used to define what the patient is to do during the therapy session. This information is preferably stored in a temporary file and in the illustrated embodiment, this temporary file is stored on the program disk 220*a* and is given a name that includes the patient's unique I.D. number followed by the extension "TMP" to indicate to the system that this is a temporary file that is to be read whenever the patient begins a therapy session in order to obtain the session parameters. Once this file has been created, the system appends the patient name to a file of patients that is scheduled for therapy on a given day. To facilitate its operation, the names file is given a name that includes the date of the scheduled therapy session. For example, the format of the file name for the names file may be "YYMMDD.NMS" where "YY" are the right two digits of the year of the therapy session, "MM" is the month and "DD" is the day of the therapy session. The session monitoring program 234 is then activated to begin a therapy session for one or more patients. At a prearranged time, or appointment, the operator initiates the therapy session by entering the patient's name or selecting a patient from a list of names stored in the YYMMDD.NMS file. Selection of the patient causes a command signal to be sent to the base station which then dials up the patient and establishes a telephone link between the base station and the patient unit 40. The session monitoring program 234 reads the temporary and permanent patient file for that patient to determine the session parameters and then issues commands that activate the patient unit 40 to begin transmitting both patient voice signals and physiological data to the base unit 20. The session monitoring program also opens a data file on the dedicated hard disk 220*b* which stores the physiological data as it is received by the base unit. It is important to note, that with the current system all physiological data transmitted by the patient station 40 is stored on the dedicated hard disk 220*b* in a patient file for the entire session. Moreover, the data is stored in real time. In the illustrated embodiment, the file for storing the physiological data is given a name that includes the patient's unique identifying number (PATIENT#) followed by the extension "D" to indicate to the system that it is a data file.

At the conclusion of the therapy session, the data editor program 236 is activated which is used to edit the physiological data stored on the dedicated hard disk 220*b* and to store all or some of the data on a removable storage media such as a "floppy disk" 240. Because of the large amounts of data stored during a therapy session, the non-removable storage media provided by the hard disk 220*b* would soon be filled if one tried to permanently store all the patient data. For this reason, the system provides for storing at least pertinent information on a floppy disk 240 so that the physiological data for a given patient stored on the hard disk 220*b* can be removed to provide space for storing the data for subsequent patients or subsequent sessions for the same patient.

In the preferred and illustrated embodiment, a patient disk 240 (which, as indicated above, may be a floppy disk) is created by the system and is used to store pertinent data recorded by the dedicated hard disk 220b during the therapy session. It should be noted, that a floppy disc may be used to store the entire therapy session but in most applications, this is unnecessary since the bulk of the data recorded for most patients will comprise normal ECG data. Whenever a patient disk is created, the system stores a copy of the patient's permanent data file (PATIENT#.PMT, which is created by the patient scheduling program 232). In addition, for each session, the associated temporary file (YYMMDD.TMP) is also stored on the patient disk. In the preferred operation, after the temporary file is copied to the patient disk (at the conclusion of the therapy session), it is erased from the hard disk 220b.

If the physiological data being collected and stored is ECG data, the operator can selectively review the patient's ECG data and save any number of predetermined ECG data intervals to the patient disc. This data is stored in a report file which in the disclosed embodiment has a file name in the form of "YYMMDD.RPT". As explained above, the first six characters of the name indicate the date of the therapy session and the extension "RPT" tells the system that this is a report file containing physiological data selected by the operator for permanent storage.

In the disclosed embodiment, the data editor program 236 also scans the entire patient data file (PATIENT#.D) to review all of the physiological data stored for the session. If the system includes means for detecting abnormal physiological data such as "arrythmia" in ECG data, this information is recorded on the patient disk 240. For example, if arrhythmia is detected in ECG data, a portion of the ECG data before and after the arrhythmia detection would be recorded on the patient disk so that it can be reviewed at a later date if necessary.

When the session data editor program is exited, the report generator program 238 would normally be called-up to provide a hard copy print-out (on a printer 28) summarizing the data received during the therapy session. The report may include information regarding pulse rate, blood pressure as well as a print-out of the physiological data selected by the operator. For example, if ECG data is being monitored, the rhythm charts selected by the operator would form part of the report.

In addition, the report generator may be used to produce trend reports to show a patient's progress over several sessions. To use this feature, the data for several therapy sessions would be read from one or more floppy disks. The report generator then processes all of the retrieved data to produce a composite report to show a patient's progress over an extended period of time.

Figure 9:
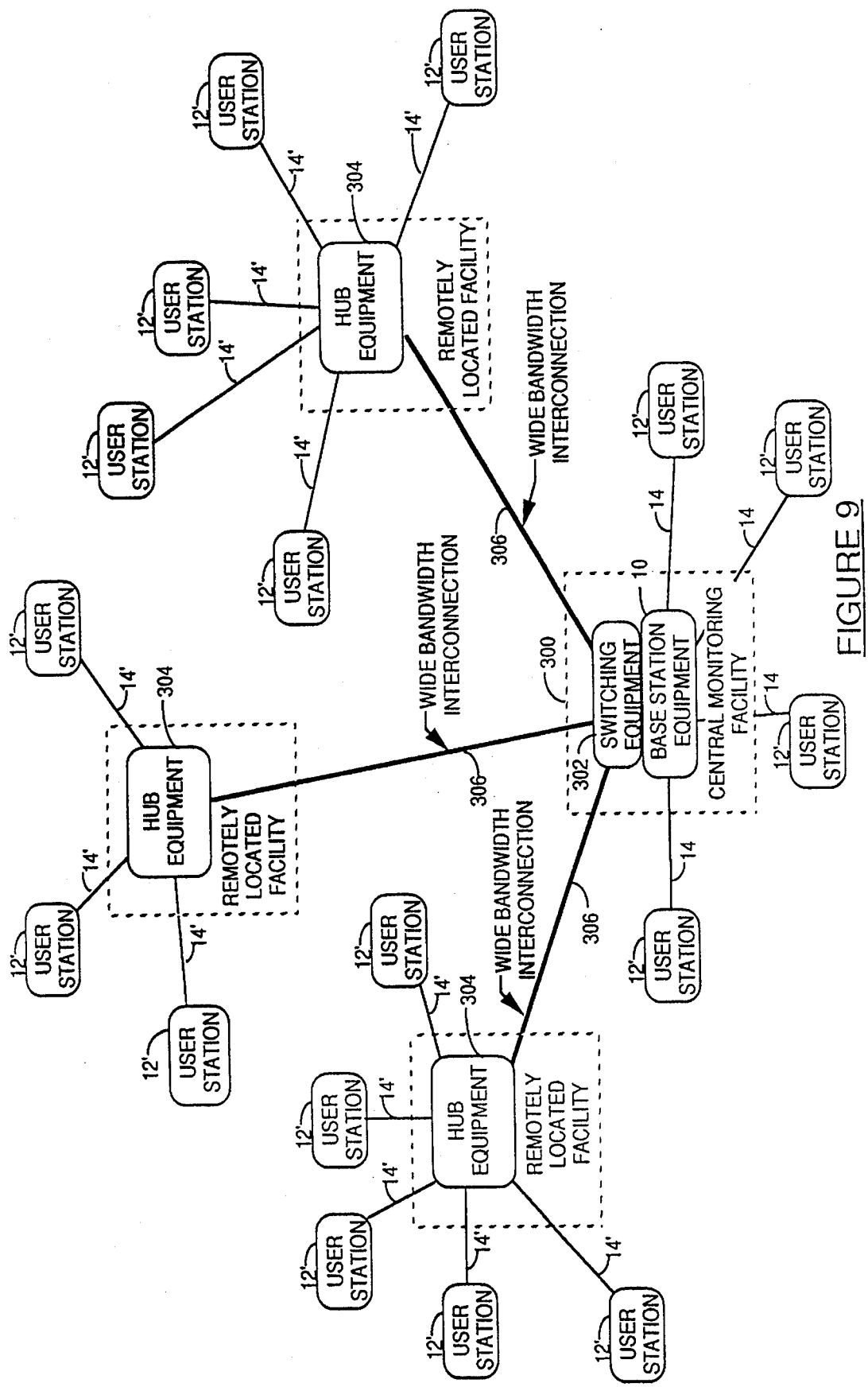

FIG. 9 illustrates a more advanced embodiment of the present invention. In the FIG. 9 embodiment, the base station 10 is located at a central monitoring facility 300. Through the use of switching equipment 302, the base station 10 communicates with a plurality of satellite stations or hubs 304 over a wide band width telephone line 306. Each satellite station or hub 304 communicates with a plurality of user stations 12' over conventional local phone lines 14'. It should be noted in FIG. 9, that the base station 10 also communicated directly with user stations 12 over local phone lines 14.

In this disclosed embodiment, equipment usage is maximized and more importantly, it enables extreme remote locations to provide exercise monitoring under the supervision of competent professionals without requiring the purchase of an entire system (or the hiring of the necessary personnel. For example, small rural hospitals could provide what appeared to patients to be a locally monitored therapy session when in fact the rural hospital would only have the hub equipment. The hub would communicate with the base station over the wide band width telephone line 306. This same type of arrangement can also be employed in a wide area physical fitness program. The hubs 304 would communicated with groups of participants over voice grade phone lines 14'. A single base station 10, manned by professional personnel would in turn receive the data from the satellite stations 304.

Although the invention has been described with a certain particularity, it should be understood that those skilled in the art can make various changes to it without departing from the spirit and scope as hereinafter claimed.

We claim:

1. An exercise monitoring system comprising:
   a) a user station including:
      i) means for monitoring activity of a user during an exercise session, including means for modulating a carrier having a predetermined frequency in the range of about 2000 Hz to about 2600 Hz with a non-digitized analog physiological waveform to produce a modulated analog, physiological signal having a predetermined frequency band during the exercise session;
      ii) voice communication means for transmitting voice signals having a predetermined frequency range from said user to a transmitting means forming part of said user station;
      iii) said predetermined frequency range of said voice signals being substantially wider than said predetermined frequency band of said physiological signal and said predetermined physiological signal frequency band being located between upper and lower limits of said voice signal predetermined frequency range but not including said limits;
      iv) signal combining means for combining said physiological signal with said voice signals to produce a composite, analog signal that is transmittable by said transmitting means to a remote location, including means for removing a portion of said voice signals that are within said predetermined frequency band of said physiological signal prior to combining said voice signals with said physiological signal;
   b) a base station for receiving said composite, analog signal from said transmitting means, said base station including signal separating means for separating said voice signals from said physiological signal.

2. The system of claim 1 wherein said user station includes means for receiving a voice signal from said base station and concurrently transmitting physiological data and voice signals to said base station.

3. The system of claim 2 wherein said composite signal has a frequency range of from approximately 400 Hz to 3400 Hz.

4. The system of claim 1 wherein said base station includes means for a receiving multiple composite signals, concurrently, from a plurality of remote user stations.

5. The system of claim 4 further comprising means for receiving and monitoring physiological data transmitted from local user stations.

6. The system of claim 1 wherein said means for monitoring comprises an ECG monitor for generating ECG data as part of the physiological data.

7. The system of claim 1 further comprising an exercise device located at the user station and said system includes means for monitoring work output of the user on said exercise device and providing workload data to the signal combining means.

8. The system of claim 1 wherein said base station includes means for storing all of the physiological data transmitted by said user unit during an exercise session.

9. The apparatus of claim 8 wherein said means for storing all of said physiological data comprises a mass storage device and said base station further comprises means for transmitting at least portions of said physiological data received during a exercise session to a storage medium that is removable from said base unit.

10. The system of claim 9 wherein said mass storage device comprises a dedicated hard disk.

11. The system of claim 1 wherein said physiological data monitored by said monitoring means is conveyed to said transmitting means by a fiber optic cable.

12. The system of claim 1 wherein said means for conveying said composite signal from said user station to said base station comprises a voice grade phone line.

13. The system of claim 1 wherein said predetermined frequency range of said voice signals is approximately 400 Hz to 3400 Hz.

14. The system of claim 1 wherein said predetermined frequency band comprises substantially 2170 Hz–2370 Hz.

15. The system of claim 1, wherein said physiological data modulates a carrier that is substantially the midpoint of said predetermined frequency band.

16. The system of claim 15 wherein said carrier frequency is substantially 2270 Hz.

17. The system of claim 15 wherein said carrier frequency is within a voice frequency spectrum.

18. The system of claim 1 wherein said physiological data, monitored by said monitoring means, and said voice signals are conveyed to said transmitting means by a fiber optic cable.

19. The system of claim 1 wherein said physiological data, monitored by said monitoring means, is conveyed to said transmitting means by a signal conveying means that is substantially unaffected by electromagnetic interference.

20. The system of claim 19 wherein said signal conveying means comprises fiber optic cable.

21. The system of claim 1 wherein said predetermined frequency range comprises voice transmission frequency spectrum of a voice grade phone line.

22. The system of claim 1 wherein said exercise monitoring system forms part of a patient rehabilitation program.

23. The system of claim 1 wherein said means for removing a portion of said voice signals that are within said frequency band comprises a notch filter.

24. The apparatus of claim 23 wherein said notch filter is controlled by a filter clock, the filter clock frequency of said filter clock determining the frequency band filtered by said notch filter.

25. The system of claim 24, wherein said patient station includes a system clock having a predetermined clock frequency for driving a microprocessor means forming part of said patient station, said patient station further including means for coupling said system clock to said filter clock to synchronize said filter clock with said system clock so that said filter clock frequency is a sub-multiple of said predetermined system clock frequency.

26. The system of claim 1 wherein said means for conveying said composite signal from said user station to said base station comprises a wide bandwidth telephone line.

27. The system of claim 1 wherein said means for conveying said composite signal from said user station to said base station comprises a voice grade telephone line and a wide bandwidth telephone line.

28. The system of claim 1 wherein said base station includes means for receiving multiple composite signals, concurrently, from a plurality of remote user stations and a plurality of local user stations.

29. The exercise monitoring system of claim 1, further comprising means forming part of said base station for sending voice signals from said base station and, further including means forming part of said user station for receiving the voice signals transmitted by said base station.

30. A method for sending a non-digitized waveform containing physiological or other analog data and a voice signal, concurrently, over a voice grade phone line, comprising:

a) establishing a predetermined frequency band intermediate a voice frequency range of 400 Hz to 3400 Hz;

b) removing voice signals having frequencies that are within said predetermined frequency band from a speech signal to produce a filtered speech signal;

c) modulating, using frequency modulation, a carrier which is substantially a mid-frequency in said predetermined frequency band with said non-digitized analog physiological waveform to produce a frequency modulated analog signal; and d) combining said filtered speech signal with said frequency modulated analog signal to produce a composite analog signal.

31. The method of claim 30 where in addition to the physiological data, workload data is encoded into the predetermined frequency band.

32. A method for sending a non-digitized, physiological waveform signal and a voice signal, concurrently, over a voice grade phone line, from a user station to a base station, comprising:

a) establishing a predetermined frequency band intermediate a voice frequency range of 400 Hz to 3400 Hz, said predetermined frequency band being in the range of about 2000 Hz to about 2600 Hz;

b) filtering a speech signal to remove signals within said predetermined frequency band from said speech signal, while leaving speech signals above and below said predetermined frequency band substantially unaffected;

c) modulating, using frequency modulation, a carrier frequency which is substantially a mid-frequency in said predetermined frequency band with said non-digitized, physiological waveform signal to produce a frequency modulated signal; and, d) combining said filtered speech signal with said frequency modulated signal to produce a composite analog signal.

33. A method of concurrently transmitting, without substantial distortion, a non-digitized, analog ECG signal in a range of 0.05 Hz to 100 Hz within a voice signal over a voice grade telephone line having a frequency range of 400 to 3400 Hz without noticeable loss of intelligibility and quality comprising the steps of:

a) selecting a carrier frequency in a range of from about 2000 to about 2600 Hz;

b) modulating the selected carrier frequency by the non-digitized analog ECG signal to create a modulated carrier having a predetermined frequency range;

c) filtering from the frequency range of voice transmission signal a frequency band corresponding to the frequency range of the modulated carrier;

d) mixing the ECG modulated carrier with the filtered voice signal to form a composite voice-ECG analog signal such that said non-digitized, analog ECG signal is transmitted within said voice signal;

e) transmitting the composite voice-ECG analog signal to a receiving station over a voice grade line having a frequency range of about 400 to about 3400 Hz;

f) separating the ECG modulated carrier and the filtered voice signal from the transmitted voice-ECG analog signal; and g) demodulating the modulated carrier frequency to create a facsimile of the original ECG analog signal.

* * * * *